United States Patent [19]

Nagasaki et al.

[11] Patent Number: 4,618,885
[45] Date of Patent: Oct. 21, 1986

[54] ELECTROMAGNETIC NOISE PREVENTIVE MEANS FOR AN ENDSCOPE WITH SOLID STATE IMAGE PICKUP ELEMENT

[75] Inventors: Tatsuo Nagasaki, Musashino; Hiroyoshi Fujimori, Hachioji, both of Japan

[73] Assignee: Olympus Optical Co., Ltd., Tokyo, Japan

[21] Appl. No.: 647,513

[22] Filed: Sep. 5, 1984

[30] Foreign Application Priority Data

Sep. 5, 1983 [JP] Japan .................. 58/163600

[51] Int. Cl.$^4$ .................. A61B 1/04; A61B 17/39
[52] U.S. Cl. .................. 358/98; 128/4; 128/303.15; 358/167
[58] Field of Search .................. 358/98, 167, 11, 21 R; 128/3-8, 303.15

[56] References Cited

U.S. PATENT DOCUMENTS

| 3,984,629 | 10/1976 | Gorog | 358/167 |
| 4,051,516 | 9/1977 | Weston | 358/11 |
| 4,487,489 | 12/1984 | Takamatsu | 128/6 |
| 4,517,976 | 5/1985 | Murakoshi | 128/303.15 |
| 4,519,391 | 5/1985 | Murakoshi | 128/303.15 |

FOREIGN PATENT DOCUMENTS

| 69530 | 4/1983 | Japan . |
| 69528 | 4/1983 | Japan . |

Primary Examiner—Britton Howard W.
Attorney, Agent, or Firm—Armstrong, Nikaido, Marmelstein & Kubovcik

[57] ABSTRACT

In this invention, the spectral structure of the high-frequency current generated by the cauterizing power circuit for high-frequency incision and excision tools is set in the frequency interleave relationship with the comb-shaped spectral structure inherent in the picture signal formed by the solid pickup element, when an affected part of a subject is collected using the high-frequency incision and excision tools together with an endscope with the solid pickup element. The picture signal, output form the solid pickup element, is supplied to the display unit via a comb line with the characteristics to meet its spectral structure to become the signal without the spectrum component (noise) caused by the high-frequency current from the said cauterizing power circuit.

3 Claims, 7 Drawing Figures

ELECTROMAGNETIC NOISE PREVENTIVE MEANS FOR AN ENDSCOPE WITH SOLID STATE IMAGE PICKUP ELEMENT

BACKGROUND OF THE INVENTION

This invention concerns a noise preventive equipment for an endoscope which makes it possible to display a true and clear image of a subject on the display unit while preventing the high-frequency current from the cauterizing power circuit used to drive high frequency incision and excision tools from giving noise to the picture signal obtained by the solid state pickup element when the endoscope using a solid state pickup element is used together with high frequency incision and excision tools.

Conventionally used medical endoscopes consist of a hard type endoscope with a hard and semi-linear inserting member and a soft type endoscope with a soft inserting member which can be inserted into a human body through the mouth. These endoscopes have an image forming optical system consisting of an objective lens which observes inside of the body and forms an image, at the end of the inserting member. With this image forming optical system which sends the formed inside image to the end of the image guide on the operating unit end through the channel of an optical fiber bundle called an image guide, the image inside the subject can be observed through the eye lens. From the operating unit, illuminating light from the light source equipment is irradiated to the subject through a light guide cable consisting of the same optical fiber bundle. Furthermore, the inserting member of the endoscope has a channel to introduce therethrough a forceps, high-frequency scalpel, etc. from the operating unit to the end of the inserting member so that the medical treatment and biopsy can be performed while observing with the endoscope.

Owing to the recent progress of electronics, such solid state pickup elements as a CCD (Charge Coupled Device), a BBD (Bucket Brigade Device) and a MOS type sensor which can capture the image as an electrical signal have been developed, and these solid state pickup elements are being used at the end of the inserting member of the endoscope.

But when the high-frequency cauterization and excision surgery and biopsy are conducted with an endoscope using such a solid state pickup element and high-frequency incision and excision tools (hereinafter called high-frequency scalpel), the high-frequency current from the cauterizing power source for the high-frequency scalpels is read by the scanning solid state pickup element and superimposed as noise on the picture signal, thus making the picture displayed on the display unit indistinct.

The frequency of the high-frequency current generated by the high-frequency scalpel is set to a value which does not affect the human body. The proper frequency is usually higher than 300 (KHz). On the other hand, the color picture signal has the frequency band of, for example, 4.3 (MHz). Therefore, the frequency band of the high-frequency current overlaps the lower band of the picture signal.

FIG. 1 is a spectrum map to show this relationship, with the axis of ordinates showing spectrum strength and axis of abscissas showing frequency, and N represents the spectrum of the color picture signal and H the spectrum of high-frequency current. When the band of the high-frequency current overlaps that of the picture signal like this, the picture displayed on the display unit becomes indistinct and what is worse, the operation must be stopped. As a measure to solve this problem, the patent application No. 69530/83 and No. 69528/83 issued by the Patent Office in Japan proposed that the portion where the high-frequency current runs be shielded and the frequency of the high-frequency current be raised to avoid the band of the frequency picture signal and the frequency of the picture signal be raised to avoid the frequency band of the high-frequency current, but both of them are not able to remove positively the high-frequency current, the cause for the noise, from the picture signal.

BRIEF SUMMARY OF INVENTION

The objective of this invention is to provide a noise preventive equipment for an endoscope which makes it possible to display a clear subject image by removing positively the noise only from the noise-superimposed picture signal instead of shielding the signal line of the picture signal from the noise from the high-frequency scalpel, etc.

Another objective of this invention is to provide noise preventive equipment for an endoscope which makes it possible to display a subject image true to the original image by removing the noise component from the noise-superimposed picture signal without having any adverse effect on the spectrum of the picture signal.

Still another objective of this invention will be made clear from the embodiments to be described later.

DETAILED DESCRIPTION

First of all, the embodiment 1 of this invention will be explained referring to FIG. 2.

Figure 2:
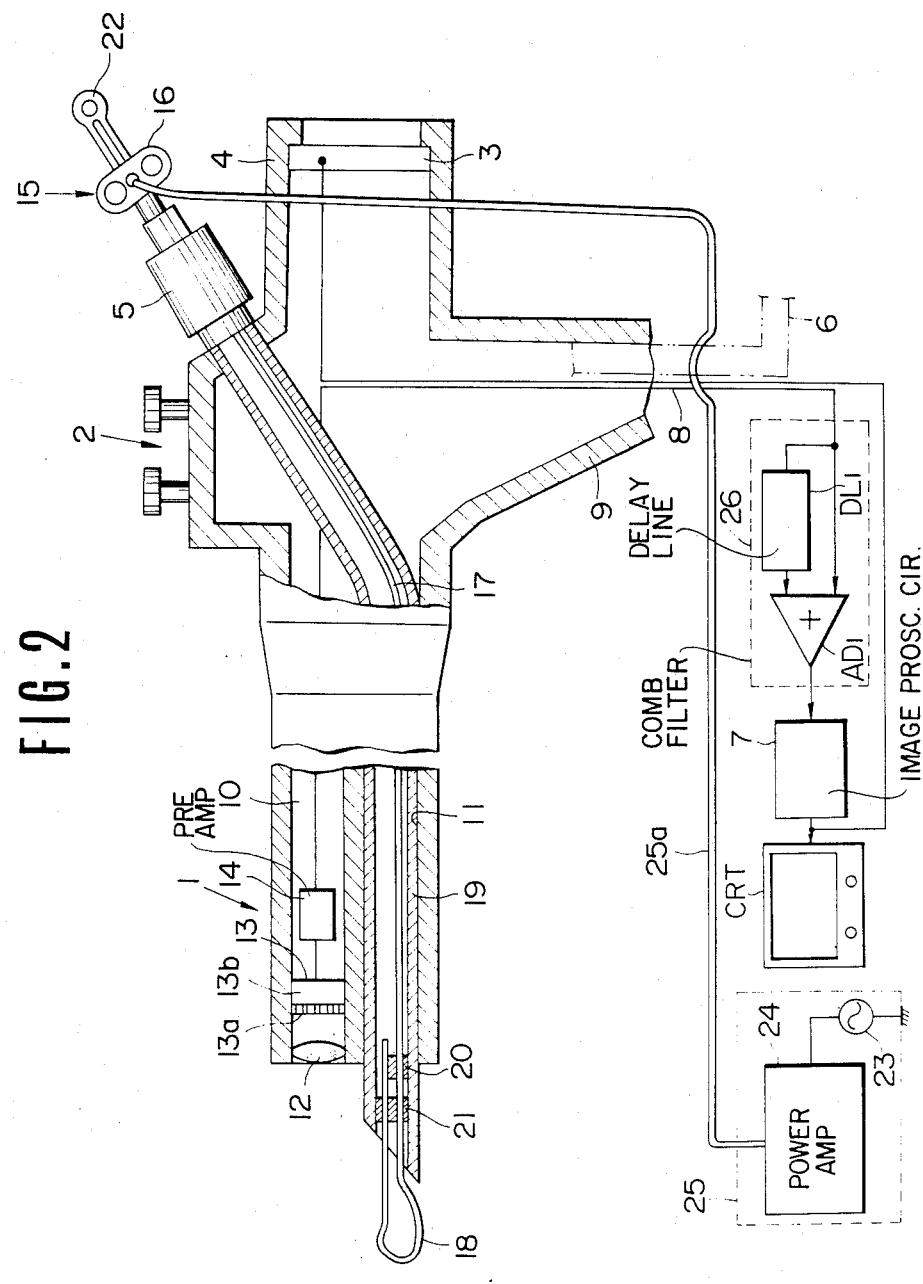
FIG. 2 is a circuit diagram to show the noise preventive equipment for an endoscope related to the first embodiment of this invention.

In FIG. 2, the endoscope proper consists of an inserting member including an end portion 1 of the inserting member and a manual operating unit 2 and the manual operating unit 2 is provided with an eye lens part 4 with a liquid crystal panel 3 on which can be observed the subject image. The operating manual unit 2 has a derivation part 9 which introduces the forceps and scalpel inserting member 5 on the upper side and light guide cable 6 and signal line 8 for inside image signal on the lower side to the outside of the main body.

The end portion 1 of the inserting member has a signal channel 10, a channel 11 for forceps and scalpel and a light guide channel for light guide cable 6. These signal and scalpel channels 10 and 11 are connected to the manual operating unit 2.

The signal channel 10 is provided with an objective lens 12 at the end opening of the end portion 1 of the inserting member. At the rear of this objective lens 12, for example, a CCD solid state pickup element 13 consisting of a photoelectric converter 13a and an accumulator/reader 13b is provided, and the subject image formed by the objective lens 12 is irradiated to the photoelectric converter 13a of the solid state pickup element 13 and stored in the accumulator/reader 13b. This accumulator/reader 13b is connected to the preamplifier 14 and the read-out picture signal is introduced out to the signal therefrom line 8. The driving signal to control the supply voltage to drive the preamplifier 14 and operation of the solid state pickup element 13 is supplied from the image processing circuit 7, but the supply passage is omitted in the drawing.

The aforementioned signal line 8 is connected to the comb line filter 26 which consists of 1 H (H is one horizontal scanning period) delay line $LD_1$ and adder $AD_1$. The outlet end of this comb line filter 26 is connected to the image processing circuit 7 which converts the picture signal passing through the comb line filter 26 into a display signal and supplies it to the CRT. The display signal is also supplied to the liquid crystal panel 3 of the eye lens part 4. The driving signal consists of the basic clock pulse which is set from the relationship between the horizontal frequency of 15.75 KHz and number of picture elements, for example, in the case of a frame transfer type CCD pickup element, it consists of an accumulator driving pulse to store the inside image as charges into the accumulator/reader 13b from the photoelectric converter 13a corresponding to 1 frame period of the display signal and the transfer driving pulse to transfer and read signals from the accumulator/reader 13b to the output side. This transfer driving pulse is of a frequency which is an integral number of times the horizontal frequency and determines the spectrum structure of the picture signal.

The high-frequency scalpel 15 consists of a handle end 16, high-frequency transmission line 17 and scalpel 18 which forms one loop with the high-frequency transmission line 17, and the high-frequency transmission line 17 is coated with flexible sheath 19. In order to load the high-frequency scalpel 15 into the endoscope, the end of the sheath 19 is inserted from the forceps and scalpel inserting member 5, passed through the passage (not illustrated) within the operating unit 2, and introduced into the channel 11 for forceps and scalpel of the end portion 1 of the inserting member, and then the sheath 19 of high-frequency scalpel 15 is projected from the end surface of the inserting member.

From the end of this sheath 19, the scalpel 19 is projected. This sheath 19 is provided with a stopper ring 21 inside the end thereof, and at the rear of the stopper ring 21, a slider 20 which freely moves in the sheath 19 is provided.

The aforementioned high-frequency transmission line 17 is inserted through these slider 20 and stopper ring 21, and the end of the loop-like scalpel 18 is fixed to the stopper ring 21. The slider 20 can be moved in the sheath 19 by moving the knob 22 on the handle end 16 of the high-frequency scalpel 15, and when the slider 20 is stopped by hitting the stopper 21, the loop of the scalpel 18 becomes largest, and then, by hitching the affected part of the subject with the loop and pulling the knob 22, the slider 20 is retreated to make the loop smaller, thus gripping the affected part.

The high-frequency scalpel 15 is driven by the cauterizing power circuit 25 consisting of high-frequency signal source 23 and power amplifier 24. The high-frequency signal source 23 of the power circuit 25 is a kind of oscillator and the oscillated frequency is set to n/2 (n is an odd number) times of the repeated frequency (horizontal frequency) of the spectrum of the picture signal obtained by the solid state pickup element 13.

Figure 1:
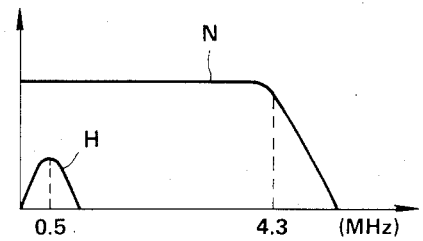
FIG. 1 is a spectrum map to show the relationship between the spectral characteristic of the conventional high-frequency current and that of the picture signal.
Figure 3:
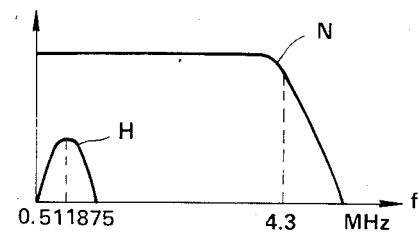
FIG. 3 is a spectrum map to show an example of the relationship between the spectral characteristic of the high-frequency current and that of a picture signal of this invention.
Figure 4:
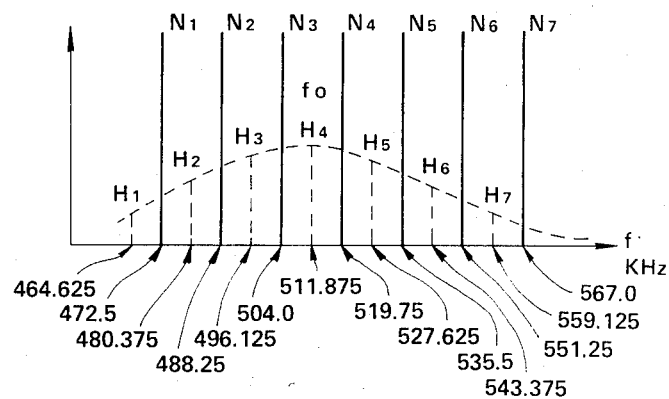
FIG. 4 is a spectrum map to show a partial enlargement of FIG. 3.

With the noise preventive equipment of the aforementioned configuration, the noise which is caused when the high-frequency current of the high-frequency scalpel 15 is superimposed on the pictue signal obtained by the solid pickup element can be removed by means of the comb line filter 26, because the spectrum of the high-frequency current of the high-frequency scalpel and that of the inside image signal creates a frequency interleave relationship, and the noise is interleaved in the valley of the picture signal spectra. Specifically, the spectrum N of the inside image signal exists in the band of 0–4.3 (MHz) and the picture signal stored in the solid state pickup element 13 has a strong spectrum at the position of an integral number of times of the horizontal frequency fH because the transfer driving pulse to read the picture signal is set to the integral number of times the horizontal frequency. Therefore, this spectrum is distributed at the repeated positions of the horizontal frequency (higher harmonics of horizontal frequency), and for example, in the area where the spectrum H of the high-frequency current overlaps, it becomes spectrum ... $N_1$–$N_7$ ... as shown in FIG. 4. In the valleys of the repeated spectra $N_1$–$N_7$, no signal component is distributed. Here the spectrum $N_1$ shows the picture signal components distributed centering around the higher harmonic No. 30 of the horizontal frequency, $N_2$ the higher harmonic No. 31, $N_3$ the higher harmonic No. 32, $N_4$ the higher harmonic No. 33, $N_5$ the higher harmonic No. 34, $N_6$ the higher harmonic No. 35 and $N_7$ the higher harmonic No. 36. If the horizontal frequency is 15.75 (KHz), the frequency of the higher harmonic No. 30 is 472.5 (KHz), the frequency of No. 31 is 488.25 (KHz), No. 32 is 504.0 (KHz), No. 33 is 519.75 (KHz), No. 34, is 535.5 (KHz), No. 35 is 551.25 (KHz) and No. B 36 is 567.0 (KHz). If, as shown in FIG. 3, the center frequency $f_0$ of the high-frequency current is set, for example, to the frequency 511.875 KHz between the No. 32 higher harmonic and No. 33 higher harmonic, the spectrum H of the high-frequency current distributed centering on this center frequency $f_0$ is normally distributed as $H_1$–$H_7$ as shown in FIG. 4, and $H_1$ is set to the spectrum 464.625 (KHz), $H_2$ to 480.375 (KHz), $H_3$ to 496.125 (KHz), $H_4$ to $f_0$, $H_5$ to 527.625 (KHz), $H_6$ to 543.375 (KHz) and $H_7$ to 559.125 (KHz).

In such case, the relationship between the horizontal frequency fH and center frequency $f_0$ is:

$$f_0 = fH/2 \times 65 \qquad (1)$$

and the center frequency of the high-frequency current is set to 65 times of ½ of the horizontal frequency. Therefore, if the high-frequency current with such spectrum is induced (as crosstalk) into the signal line 8, the high-frequency noise conforming to the spectrum of the high-frequency current is superimposed on the picture signal, and the high-frequency noise can be removed by means of the comb line filter 26.

Figure 5:
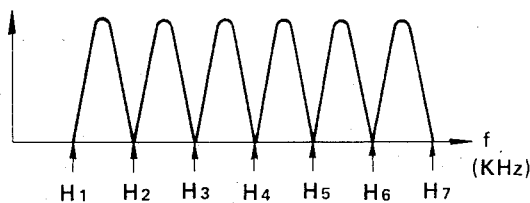
FIG. 5 is a characteristic diagram to show the frequency characteristic of the comb line filter used in the embodiment 1 of this invention.
Figure 6:
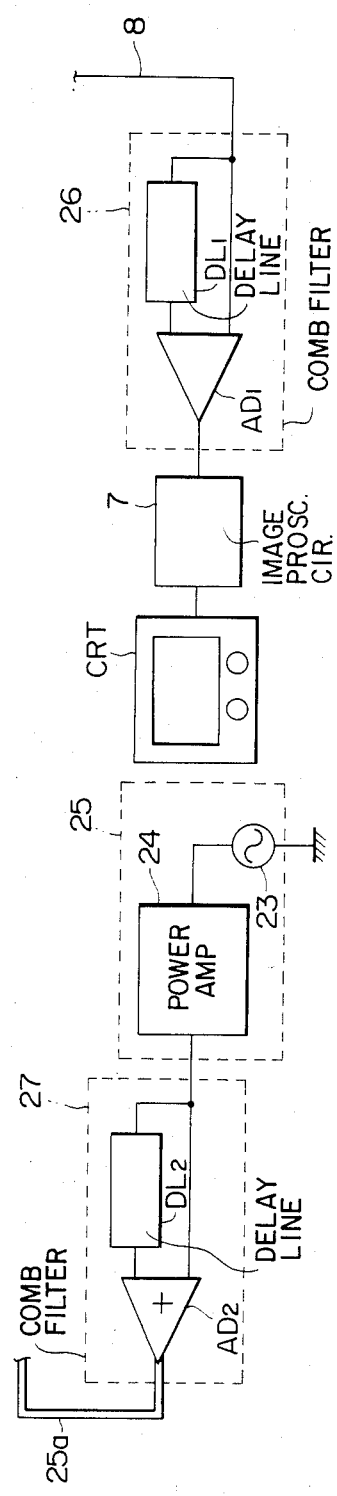
FIG. 6 is a circuit diagram to show the noise preventive equipment for an endoscope related to the second embodiment of this invention.

FIG. 5 shows the frequency characteristic of the comb line filter 26 and the axis of ordinates and axis of abscissas show frequency and response respectively. This comb line filter 26 is characterized in that it has the response valleys at the high-frequency spectra . . . $H_1$–$H_7$, and the picture signal spectrum N can pass. If the center frequency $f_0$ of the high-frequency current is set within the range with less effect on the subject picture signal, for example, to 511.875 (KHz), the high-frequency noise superimposed on the picture signal can be removed. The center frequency $f_0$ can be any value to satisfy the above formula (1) so long as the safety is confirmed and it is the frequency at the position where the picture signal spectrum does not exist. FIG. 6 shows the embodiment 2 of this invention in which the distribution of the high-frequency current spectra is forcefully brought into conformity with the valleys of the picture signal spectra. In this figure the endoscope proper and high-frequency scalpel are omitted, and for the same parts in FIG. 2, the same symbols are used.

Figure 7:
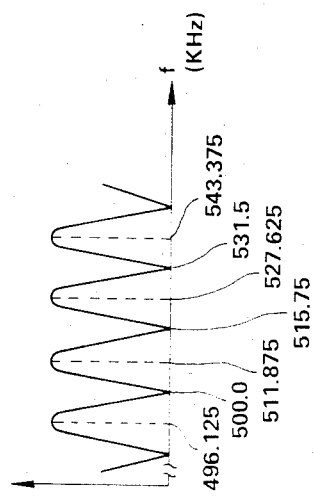
FIG. 7 is a characteristic diagram to show the characteristic of the comb line filter to be provided on the cauterizing power source side in the embodiment of this invention.

In FIG. 6, the comb line filter 27 provided on the output side of the power amplifier 24 consists of 1H delay line $DL_2$ and adder $AD_2$, and the frequency is set, as shown in FIG. 7, so that the response valleys come to such frequencies as 500.0 (KHz), 515.75 (KHz), 531.5 (KHz) . . . . If the spectrum of the high-frequency current is limited in advance to such frequency components as 496.125 (KHz), 511.875 (KHz), 527.625 (KHz), 543.375 (KHz) . . . using the comb line filter 27 on the high-frequency scalpel side, the high-frequency noise to be superimposed on the picture signal will be only the noise of these frequency components and the said frequency components as noise can be removed by means of the comb line filter 26 on the endoscope side.

As aforementioned, in this invention, the noise from the high-frequency scalpel which is superimposed on the picture signal is removed using the comb line filter, thus making it possible to remove only the noise component without losing the signal component necessary for display and to obtain a clear picture true to the original image formed by the solid state pickup element.

It is of course possible to form many other embodiments without conflicting with the spirit and scope of this invention and this invention is not limited to the particular embodiments except the limitations stated in the claims. It is of course possible to apply this invention to the endoscope with the solid state pickup element provided on the operating unit side. The liquid crystal panel 3 provided in the eye lens part 4 is not always necessary.

We claim:

1. A noise eliminating device for an endoscope having a current source means for actuating a high frequency scalpel and an image indicating means for displaying image signals from a solid state image pickup element in the endoscope, said noise eliminating device comprising:

an adjusting means for adjusting the spectrum of the high frequency current of said current source means for said high frequency scalpel, wherein said adjusting means adjusts the frequency band of the high frequency current to coincide with an image signal band, and the frequency spectrum of the high frequency current overlaps with the frequency spectrum of a driving pulse for reading an image signal from said solid state image pickup element, and wherein the frequency of the driving pulse for reading the image signal from said solid state image pickup element corresponds to an integral multiple of an image horizontal frequency $f_H$; and a comb filter means coupled to said image indicating means for removing high frequency noise generated by said current source means from the image signal of said solid state image pickup.

2. A noise eliminating device for an endoscope according to claim 1, wherein said adjusting means adjusts the central frequency $f_O$ of the high frequency current of said high frequency scalpel such that $f_O = f_H/2 \times 65$ with the horizontal frequency $f_H$ of the image signal spectrum and the respective harmonic components of the high frequency current coinciding with the clearance of the spectrum of the image signal of said solid state image pickup element.

3. A noise eliminating device for an endoscope according to claim 1, wherein said adjusting means is coupled to said current source means such that the distribution of the spectrum of the high frequency current overlaps with the clearance of the spectrum of the image signal of said solid state image pickup element.

* * * * *